United States Patent
Ye et al.

(10) Patent No.: US 11,441,421 B2
(45) Date of Patent: Sep. 13, 2022

(54) MEASURING THE OIL CONTENT IN OIL-BASED DRILLING FLUIDS

(71) Applicant: Halliburton Energy Services, Inc., Houston, TX (US)

(72) Inventors: Xiangnan Ye, Cypress, TX (US); Dale E. Jamison, Humble, TX (US); Li Gao, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 308 days.

(21) Appl. No.: 16/612,676

(22) PCT Filed: Dec. 27, 2018

(86) PCT No.: PCT/US2018/067702
§ 371 (c)(1),
(2) Date: Nov. 11, 2019

(87) PCT Pub. No.: WO2020/139351
PCT Pub. Date: Jul. 2, 2020

(65) Prior Publication Data
US 2021/0047922 A1 Feb. 18, 2021

(51) Int. Cl.
*E21B 49/08* (2006.01)
*G01N 27/02* (2006.01)
(Continued)

(52) U.S. Cl.
CPC .......... *E21B 49/08* (2013.01); *G01N 27/026* (2013.01); *G01N 33/28* (2013.01); *C09K 8/36* (2013.01)

(58) Field of Classification Search
CPC ...... E21B 49/08; G01N 27/025; G01N 33/28; G01N 33/2823
(Continued)

(56) References Cited

U.S. PATENT DOCUMENTS 7,049,831 B2 * 5/2006 Wooton ............. G01N 33/2888
324/698
2006/0214671 A1 9/2006 Wooton et al.
(Continued)

FOREIGN PATENT DOCUMENTS

WO 2018038717 3/2018
WO 2018217450 11/2018

OTHER PUBLICATIONS

Patil et al. Experimental Study of Electrical Properties of Oil-Based Mud in the Frequency Range From 1 to 100MHz), Society of Petroleum Engineers, Sep. 2010 SPE Drilling & Completion (Year: 2010).*

(Continued)

*Primary Examiner* — Nimeshkumar D Patel
*Assistant Examiner* — Jean F Morello
(74) *Attorney, Agent, or Firm* — Tenley Krueger; C. Tumey Law Group PLLC (57) ABSTRACT

Systems and methods for measurement of the oil content in oil-based drilling may be provided in accordance with embodiments of the present disclosure. A method for measuring oil content of an oil-based drilling fluid may include providing a sample of the oil-based drilling fluid. The method may further include performing electro impedance spectroscopy on the sample by a process that comprises applying an alternating electric current to the sample and measuring a response of sample to obtain electro impedance spectroscopy measurements. The method may further include determining an estimate of the oil content of the sample based, at least partially on the electro impedance spectroscopy measurements.

20 Claims, 7 Drawing Sheets

(51) Int. Cl.
*G01N 33/28* (2006.01)
*C09K 8/36* (2006.01)

(58) Field of Classification Search
USPC .................................................. 73/152.42
See application file for complete search history.

(56) References Cited

U.S. PATENT DOCUMENTS

| 2014/0062489 A1* | 3/2014 | Pindiprolu ............. G01N 13/00 |
| | | 324/347 |
| 2015/0211350 A1 | 7/2015 | Norman et al. |
| 2017/0090060 A1 | 3/2017 | Donderici et al. |
| 2018/0163537 A1* | 6/2018 | Rahaliou ............... G01N 27/026 |
| 2018/0202246 A1* | 7/2018 | Kleinguetl ............... C09K 8/02 |
| 2019/0227048 A1* | 7/2019 | Ye ........................ G01N 27/026 |

OTHER PUBLICATIONS

Perini et al. "Electrochemical Impedance Spectroscopy for in situ petroleum analysis and water-in-oil emulsion characterization." Fuel 2012; vol. 91(1): pp. 224-228. accessed online Mar. 23, 2022. (Year: 2012).*
ISRWO International Search Report and Written Opinion for PCT/US2018/067702 dated Sep. 25, 2019.

* cited by examiner

MEASURING THE OIL CONTENT IN OIL-BASED DRILLING FLUIDS

BACKGROUND

During the drilling of a wellbore into a subterranean formation, a drilling fluid, also referred to as a drilling mud, may be continuously circulated from the well surface down to the bottom of the wellbore being drilled and back to the well surface again. The drilling fluid may include a mixture of water, oil, additives (e.g., viscosifiers, weighting materials, emulsifying surfactants, and the like), and combinations thereof, to impart certain properties to the drilling fluid to satisfy different drilling requirements.

Certain drilling fluids may be oil-based and include an oil phase and an aqueous phase. Determining the oil content in an oil-based drilling fluid may be essential to an efficient drilling operation. The oil content is typically tracked and monitored during drilling operations. The oil content directly impacts drilling fluid performance, including stability, functionality, and efficiency. Measurement of the oil content in oil-based fluids may be challenging, for example, due to the presence of solids and emulsion.

Typically, the oil content has been measured using a technique called a retort. A retort uses a distillation unit to heat and then distill the oil and water in an oil-based drilling fluid. The volume fraction of each is then compared to the original known volume used during formulation of the oil-based drilling fluid in order to measure the changes to the oil-based drilling fluid during use. This process can take an hour or more. Further, it cannot be done in real-time on the actual oil-based drilling fluid while it is being circulated, as distillation of the entire fluid would be impractical, thus the process requires the use of a sample of small enough volume to be adequately distilled by the distillation unit in a practical amount of time. As such, the retort process is slower to perform and provides measurements that lag relative to the drilling operation. The retort measurements only illustrate the oil content of the oil-based drilling fluid when the sample was taken and cannot illustrate the oil content of the oil-based drilling fluid as it is presently being circulated. This in turn may lead to delayed correction of the oil-based drilling fluid and a reduction in the overall efficiency of the operation.

BRIEF DESCRIPTION OF THE DRAWINGS

The features and advantages of certain embodiments will be more readily appreciated when considered in conjunction with the accompanying figures. The figures are not to be construed as limiting any of the preferred embodiments.

DETAILED DESCRIPTION

The present disclosure relates to drilling operations and, more particularly, embodiments disclosed herein are directed to measurement of the oil content in oil-based drilling fluids. As will be discussed in more detail below, correlations may be developed using electrochemical impedance spectroscopy (EIS) to measure the oil content. EIS is a non-invasive technique for measuring properties of a medium as a function of angular frequency (also referred to as the excitation frequency). The systems and methods may be used to measure the oil content in a mud pit, on a rig, in a mud plant, in a laboratory, or at any other suitable location. In some embodiments, the oil content may be measured continuously in real time at the rig site while the oil-based drilling is being circulated in the wellbore. In some embodiments, a model may be developed that correlates EIS measurements to oil content using, for example, laboratory oil-based drilling fluids and, then EIS measurements of an oil-based drilling fluid from a wellbore may be applied to the model to estimate oil content.

The systems and methods may be used for measuring the oil-content of any suitable oil-based drilling fluid. Suitable oil-based treatment fluids may be in the form of an invert emulsion including an aqueous internal phase and an oil external phase. Those of ordinary skill in the art will appreciate that the oil-based drilling fluid generally should have a density suitable for a particular application. By way of example, the oil-based drilling fluid may have a density in the range of from about 7 pounds per gallon ("lb/gal") (840 kg/m$^3$) to about 20 lb/gal (2400 kg/m$^3$). In certain embodiments, the oil-based drilling fluids may have a density in the range of from about 8 lb/gal (960 kg/m$^3$) to about 12 lb/gal (1440 kg/m$^3$) or from about 12 lb/gal (1440 kg/m$^3$) to about 18 lb/gal 2160 kg/m$^3$). Those of ordinary skill in the art, with the benefit of this disclosure, will recognize the appropriate density for a particular application.

The aqueous phase may include any suitable aqueous liquid. The aqueous liquid may be from any source provided that it does not contain an excess of compounds that may undesirably affect other components in the oil-based drilling fluids. Suitable aqueous liquids may include but are not limited to, fresh water or salt water. Salt water generally may include one or more dissolved salts therein and may be saturated or unsaturated as desired for a particular application. Seawater or brines may be suitable for use in some examples. Suitable brines may be saturated or unsaturated as desired for a particular application. One or more salts may be added to water to provide a brine that includes the dissolved salt and the water. Suitable dissolved salts may include monovalent and divalent salts. Mixtures of monovalent, divalent, and trivalent salts may also be used. Suitable monovalent salts may include, but are not limited to, sodium chloride, sodium bromide, potassium bromide, potassium chloride, potassium formate cesium formate, potassium formate, and mixtures thereof among others. Suitable divalent salts may include, but are not limited to, calcium bromide, zinc bromide, calcium chloride, and mixtures thereof. In an embodiment, the brine may include calcium bromide, and/or any combinations thereof. In a non-limiting example, one salt may be used to prepare the brine. In another embodiment, multiple salts may be used to prepare the brine. The brine may be provided in any amount or concentration such as unsaturated, saturated, supersaturated, and saturated with additional solids. Further, the aqueous liquid may be present in the oil-based drilling fluid in any suitable amount. Without limitation, aqueous liquid may be present in the oil-based drilling fluid in an amount of about 1 vol. % to about 70 vol. %, about 10 vol. % to about 60 vol. %, or about 20 vol. % to about 50 vol. % based on a total volume of oil-based drilling fluid. One or ordinary skill in the art, with the benefit of this disclosure, should be able to select an appropriate amount of the aqueous liquid for a particular application.

The oil-based treatment fluid may further include an oil external phase that includes a base oil. Any suitable base oil may be used. It should be noted that the term "oil," as used herein, is not limited to a viscous liquid derived from petroleum. The term "oil," as used herein, may also refer to organic oils, synthetic oils, oils derived from petroleum products, mineral oils, the like, and/or any combination thereof. In an embodiment, suitable base oils may include, but are not limited to, light mineral oil, diesel oil, a glycol ether solvent, a hydrotreated light petroleum distillate having about 9 to 16 carbon atoms, ethylene glycol monobutyl ether, diethylene glycol monobutyl ether, an alkane, an aromatic organic compound, a cyclic alkane, a paraffin, desulfurized hydrogenated kerosene, a polyolefin, a polydiorganosiloxane, a siloxane, an ester, the like, and/or any combination thereof. The base oil may be present in the oil-based fluid treatment in any suitable amount, including but not limited to, an amount of about 10 vol. % to about 99 vol. %, about 30 vol. % to about 80 vol. %, or about 40 vol. % to about 70 vol. % based on a total weight of oil-based drilling fluid. One or ordinary skill in the art, with the benefit of this disclose, should be able to select an appropriate type and amount of the base oil a particular application.

Embodiments of the oil-based drilling fluids may have any suitable oil-to-water volumetric ratio (OWR). For an oil-based drilling fluid, the OWR is typically the ratio of the volume percent of the oil external phase to the volume percent of the aqueous liquid phase. In some embodiments, the oil-based treatments fluids may have an OWR of about 20:80 to about 95:5, or alternatively, about 40:60 to about 70:30, or alternatively, about 50:50 to about 60:40. For example, the oil-based treatments fluids may have an oil external phase to aqueous internal phase ratio of about 30:70, about 40:60, about 50:50, about 60:40, about 70:30, about 80:20, about 90:10, or about 95:5. One or ordinary skill in the art, with the benefit of this disclose, should be able to select an appropriate OWR of the oil-based drilling fluid for a particular application.

The oil-base drilling fluid may further include an emulsifying surfactant. Any suitable emulsifying surfactant for emulsifying an aqueous fluid into an oil external phase may be used. The emulsifying surfactants may include nonionic, anionic, cationic, amphoteric, and zwitterionic surfactants. Suitable emulsifying surfactants may include but are not limited to, fatty amines, ethoxylated nonylphenols, fatty acids, fatty acid esters, tall oil, oxidized tall oil, modified tall oil, rosin acid, resin acid, and combinations thereof. In an embodiment, the emulsifying surfactant may be present in the oil-based drilling fluid in an amount of about 2 lb/bbl (6 kg/m$^3$) to about 24 lb/bbl (68 kg/m$^3$), or about 4 lb/bbl (11 kg/m$^3$) to about 20 lb/bbl (57 kg/m$^3$), or about 6 lb/bbl (17 kg/m$^3$) to about 16 lb/bbl (46 kg/m$^3$). In an embodiment, the emulsifying surfactant used may be determined based on the hydrophilic-lipophilic balance "HLB" value of the emulsifying surfactant.

The hydrophilic-lipophilic balance ("HLB") of an emulsifying surfactant is a measure of the degree to which it is hydrophilic or lipophilic, determined by calculating a value based on the chemical groups of the molecule. This method is also referred to as the Davies HLB value. The advantage of this method is that it takes into account the effect of stronger and weaker hydrophilic groups. The method works as follows: $HLB=7+m*Hh-n*Hl$ where m is the number of hydrophilic groups in the molecule, Hh is the respective group HLB value of the hydrophilic groups, n is the number of lipophilic groups in the molecule, and Hl is the respective HLB value of the lipophilic groups.

The HLB model can be used for applications including emulsification, detergency, solubilization, and other applications. Typically, a HLB value will indicate the emulsifying surfactant properties, where a value of 1 to 3 indicates anti-foaming of aqueous systems, a value of 3 to 7 indicates water in oil emulsification, a value of 7 to 9 indicates wetting, a value of 8 to 28 indicates oil in water emulsification, a value of 11 to 18 indicates solubilization, and a value of 12 to 15 indicates detergency and cleaning. In an embodiment, the emulsifying surfactant used may have an HLB value of about 8 to about 28.

In addition, a weighting agent may be included in the oil-based drilling fluid. Weighting agents are typically particulate materials with a high-specific gravity. As used herein, the term "high-specific gravity" refers to a material having a specific gravity greater than 2.6. Examples of suitable weighting agents may include, but are not limited to, barite, hematite, ilmentite, manganese tetraoxide, galena, calcium carbonate, and combinations thereof. The weighting agent may be present in the oil-based drilling fluid in an amount sufficient fir a particular application. For example, the weighting agent may be included in the drilling fluid to provide a particular density. Suitable amounts of the weighting agent may include, but are not limited to, the weighting agent present in the oil-based drilling fluid in an amount up to about 50% by volume of the drilling fluid (vol %) (e.g., about 5 vol %, about 15 vol %, about 20 vol %, about 25 vol %, about 30 about 35 vol %, about 40 vol %, about 45 etc.). For example, the weighting agent may be present in the drilling fluid in an amount ranging from of about vol % to about 50 vol %, about 5 vol % to about 40 vol %, or about 20 vol % to about 40 vol %. One of ordinary skill in the art with the benefit of this disclosure should recognize the appropriate type and amount of the weighting agent for a chosen application.

Additionally, a wide variety of optional additives may be included in the oil-based drilling fluid as should be appreciated by those of ordinary skill in the art with the benefit of this disclosure. Suitable additives may include, but are not limited to, a surfactant (e.g., foamer, defoamer, wetting agent, detergent, lubricant, and corrosion inhibitor), a water softener (e.g., sodium carbonate), an oxygen scavenger, a biocide, pH adjusters, fluid loss control agents, viscosity increasing agents, a corrosion inhibitor (other than surfactant), the like, and/or any combination thereof. Optional additives may be added to the oil-based treatment fluid in any suitable amount as desired for a particular application.

As previously described, the methods and systems disclosed herein may use EIS to measure the oil content in the oil-based drilling fluid. The systems and methods may be used to measure the oil content of the oil-based drilling fluid in a mud pit, on a rig, in a mud plant, in a laboratory, or at any other suitable location. Prior to using EIS analysis to measure the oil content, one or more oil-based drilling fluids with known OWR may be analyzed with EIS to develop a model. This model should correlate EIS measurements to oil content in an oil-based drilling fluid. A sample of an oil-based drilling fluid may then be obtained and analyzed using EIS. These EIS measurements from the sample may then be applied to the model to obtain an estimate of the oil content in the oil-based drilling fluid.

An example technique for EIS analysis will now be described. EIS is an electrochemical technique in which an alternating electric current may be applied to a sample while measuring its response. The complex impedance is represented by the change of the amplitude and phase of the output signal in reference to the input signal. The sinusoidal voltage may be the input signal. The measured response (e.g., complex current measured between two terminals) may the output signal. The measured complex impedance at an angular frequency $\omega = 2\pi f$ has both real and imaginary parts as shown by equation (1) below:

$$Z(\omega) = Z'(\omega) + iZ''(\omega) \quad (1)$$

wherein $Z(\omega)$ is the measured complex impedance. $Z'(\omega)$ is the real pan (i.e., resistance) of the impedance, $Z''(\omega)$ is the imaginary part (i.e., reactance) of the impedance, and $\omega$ is angular frequency.

In some embodiments, a model may be developed that correlates EIS measurements to oil content in an oil-based drilling fluid. In EIS analysis, the phase angle may also be obtained from the real part of impedance ($Z'(\omega)$) and the imaginary part of impedance ($Z''(\omega)$) as shown by equation (2) below:

$$\theta(\omega) = \tan^{-1}(Z'(\omega)/Z''(\omega)) \quad (2)$$

The phase angle may be obtained at any suitable angular frequency ($\omega$). In some embodiments, the phase angle may be obtained at an angular frequency ($\omega$) of 20 hertz (Hz) to 5 megahertz (MHz), or from 500 Hz to 1 MHz, or from 1 kilohertz (KHz) to 2 KHz. The phase angle may be considered a function of both OWR and concentration of low-gravity solids. At certain frequency ranges, for example, a frequency range may be about 1 kHz to about 2 kHz, the low-gravity solids may have minimal impact on phase angle so that the phase angle change may be represented as a linear function of oil volume content. It should be understood that other frequency ranges may also be used. Thus, the phase angle may be described the phase angle may be described as a simple log-linear expression as follows:

$$PA(f) = A \ln(f) = B \quad (3)$$

wherein PA is the phase angle, A is the slope, B is the intercept, and f is frequency. The log-linear expression may be developed, for example, by logarithmic function fitting to EIS measurements of phase angle versus angular frequency to provide the log-linear expression of phase angle as a function of angular frequency. The slope (A) and intercept (B) of equation (3) can both be correlated with oil volume content. In some embodiments, the slope (A) may be represented as a function of oil volume content. In some embodiments, the intercept (B) may be represented as a function of oil volume content. Accordingly, the oil content as function of slope (A) and the oil content as a function of the intercept (B) may be expressed as the following general equations:

$$A = a \times \text{Oil vol \%} + b \quad (4)$$

$$B = a' \times \text{Oil vol \%} b' \quad (5)$$

wherein Oil vol % is oil volume content of the oil-based drilling fluid, A is the slope of logarithmic function fining to phase angle as function of frequency, B is the intercept of logarithmic function fitting to phase angle as function of frequency, a is a model coefficient based on equation (4), h is a model coefficient based on equation (4), a' is a model coefficient based on equation (5), b' is a model coefficient based on equation (5). Even further, the linear correlations of slope (A) and intercept (B) to oil volume content may be developed at different densities of the oil-based drilling fluid, in some embodiments, to provide a linear equation correlating oil volume content to slope (A) or intercept (B) and density. With these correlations of both slope (A) and intercept (B) to oil volume content, embodiments may then include estimating oil volume content of a sample. By way of example, a sample may be analyzed using EIS. Using the phase angle from EIS measurements, embodiments may include developing a simple log-linear expression of Equation (3) for the oil-based drilling fluid. In some embodiments, the slope (A) and/or intercept (B) may then be determined and applied to the model to estimate oil volume content of the sample.

Figure 1:
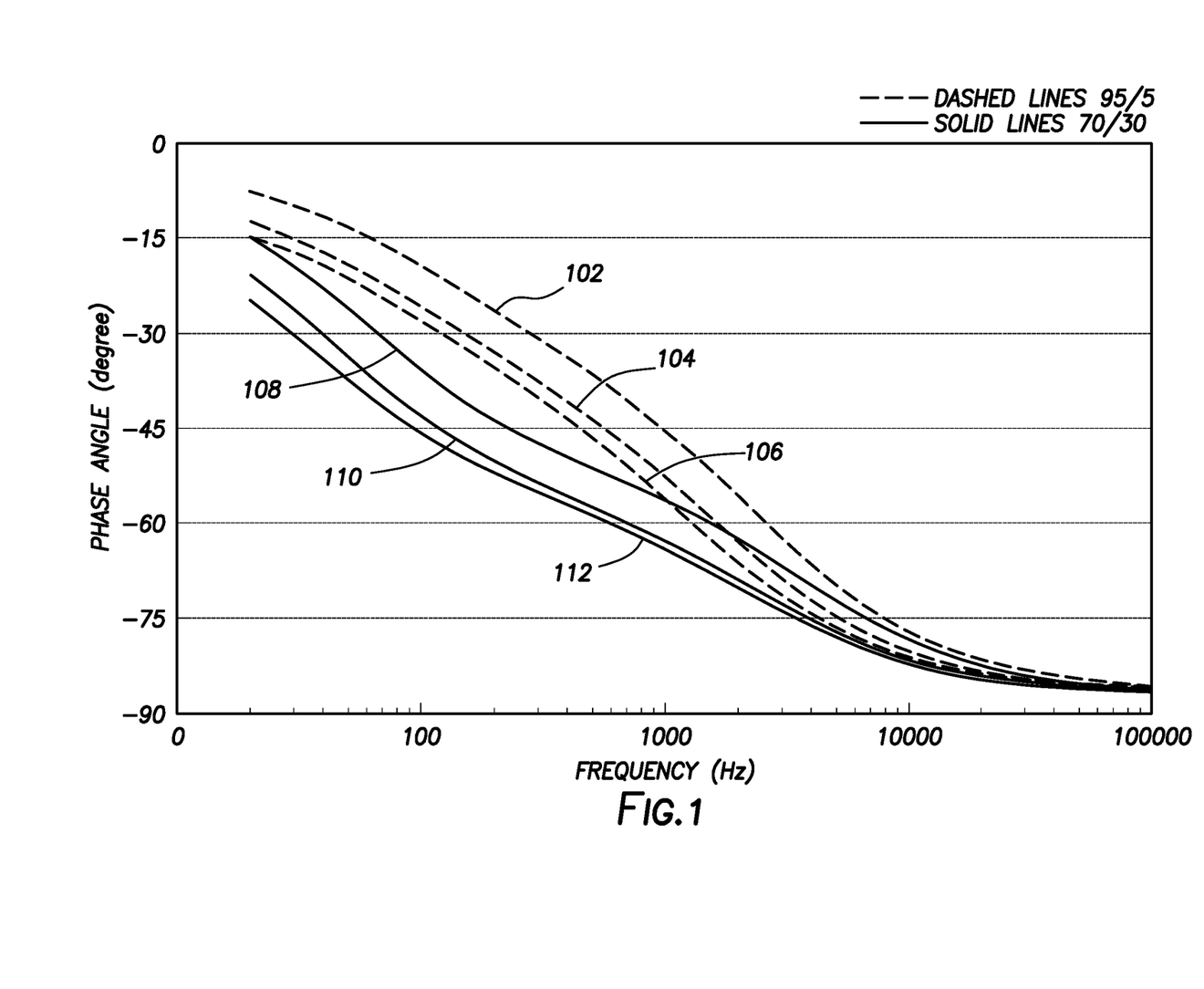
FIG. 1 is an example plot of experimental phase angle versus angular frequency for oil-based drilling fluids with different oil-to-water ratios.

An example model development will now be described in more detail with respect to FIGS. 1-4. FIG. 1 illustrates the phase angle profile for oil-based drilling fluids having various OWR. The dashed lines on FIG. 1 represent oil-based drilling fluids with an OWR of 95/5, shown as first fluid 102, second fluid 104, third fluid 106. The solids lines on FIG. 1 represent oil-based drilling fluids with an OWR of 70/30, shown as fourth fluid 108, fifth fluid 110, and sixth fluid 112. The fluids will be collected referred to as sample fluids 102 to 112. The density for each of the sample fluids 102 to 112 was 13 lb/gal (1560 kg/m$^3$). However, different amounts of low-gravity solids were included in each of the sample fluids 102 to 112, wherein the amount of REV DUST™ drill solids (ground calcium montmoriilonite clay, 2.6 specific gravity) ranged from 0 pounds per barrel to 60 pounds per barrel. As used herein, the term low gravity solids refers to materials with a low density (i.e., specific gravity of less than 3), for example, a specific gravity of 1.8 to 2.6. The concentration of low gravity solids increased from first fluid 102 to third fluid 106 and from fourth fluid 108 to sixth fluid 112. First fluid 102 and fourth fluid 108 have the same concentration of low gravity solids. Second fluid 104 and fifth fluid 110 have the same concentration of low gravity solids. Third fluid 106 and sixth fluid 112 have the same concentration of low gravity solids.

Figure 2:
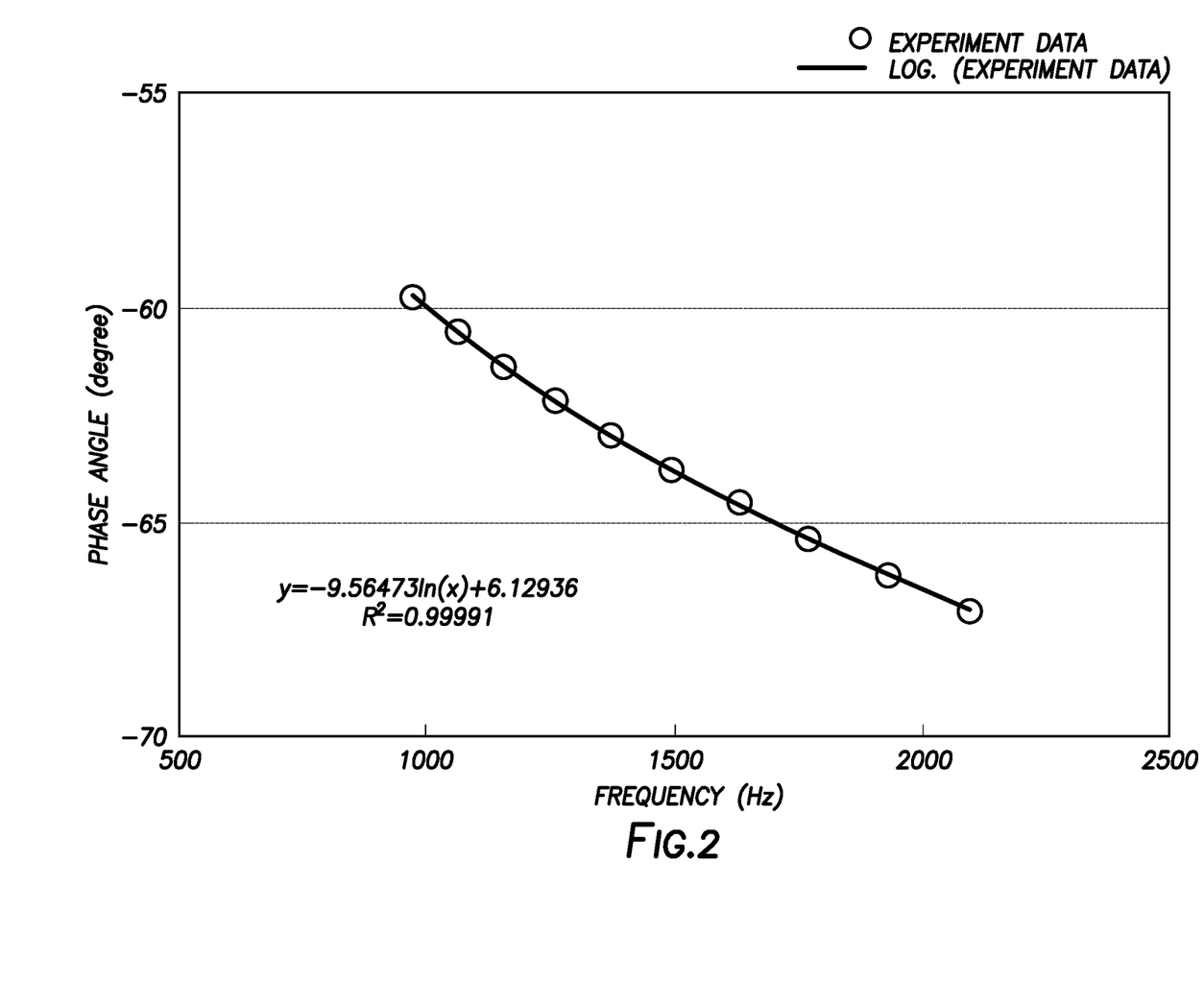
FIG. 2 is an example plot of a logarithmic function fitted to phase angle experimental data of FIG. 1 between 1 kilohertz ("kHz") to 2 kHz.

As illustrated on FIG. 1, the curves for each of each of the sample fluids 102 to 112 have similar shapes OWR the same OWR and shifts to lower frequency for increasing content of low-gravity solids. The same behavior can also be illustrated for other OWR's, thus indicating that phase angle is a function of both OWR and low-gravity solid content. As such, the absolute value of phase angle alone may not be sufficient to distinguish the contribution from OWR or low-gravity solid changes. However, the phase angle at certain ranges of frequency may not be affected by the amount of low-gravity solids in the drilling fluid. In some embodiments, this frequency range may be about 1 kHz to about 2 kHz. Thus, this rate of phase angle change may be represented a linear function of oil volume percentage. In addition, the phase angle may be described as a simple log-linear expression of equation (3) shown above. FIG. 2 illustrates fitting a logarithmic function to the phase angle experimental data between 1 kHz to about 2 kHz for a particular mud system from FIG. 1. For this example, the logarithmic function is provided by equation (6) below:

$$Y = -9.56473 \ln(x) + 6.12936 \quad (6)$$

wherein x is frequency.

Figure 3:
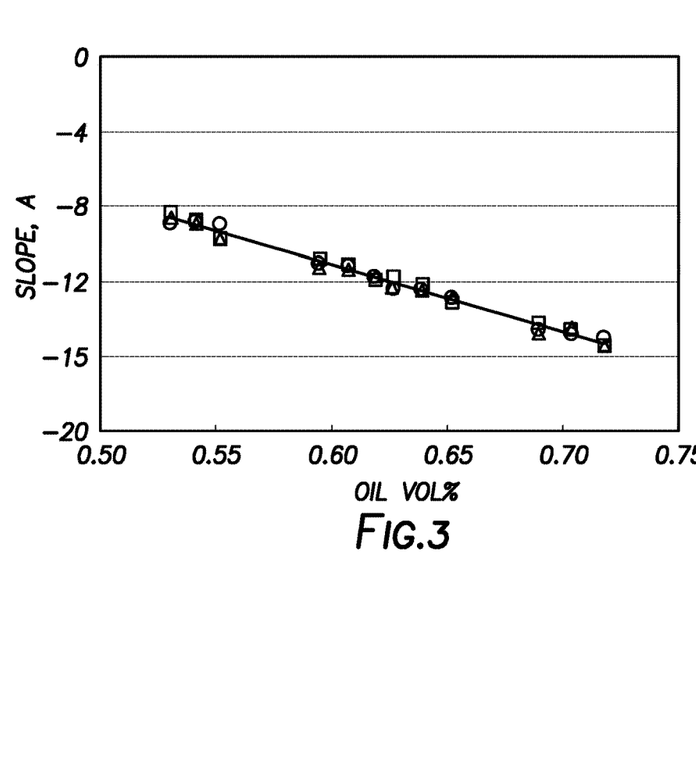
FIG. 3 is an example of slope (A) obtained from the logarithmic function fitting to phase angle of FIG. 2.
Figure 4:
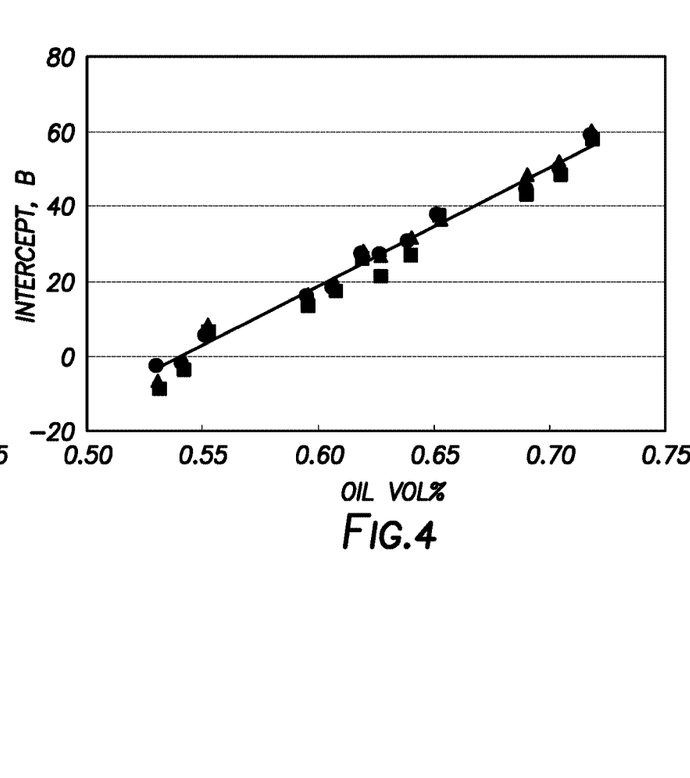
FIG. 4 is an example of intercept (B) obtained from the logarithmic function fitting to phase angle of FIG. 2.

For this log-linear expression, both the slope (A) and intercept (B) can both be correlated with oil content. FIG. 3 illustrates slope (A) as a function of oil content. FIG. 4 illustrates intercept (B) as a function of oil content. The slope (A) and intercept (B) for this example were obtained from logarithmic curve fitting to the phase angle between 1 kHz to 2 kHz. The correlations were developed for oil-based drilling fluids having a density of 13 lb/gal (1560 kg/m$^3$) and OWR ranging from 70/30 to 95/5. The low-solids content for these oil-based drilling fluids varied, wherein the amount of REV DUST™ drill solids (ground calcium montmorillonite clay, 2.6 specific gravity) ranged from 0 pounds per barrel to 60 pounds per barrel The different symbols on FIG. 3 represent different water-phase salinity: squares for 150 Kppm, triangles for 200 Kppm and circles for 250 Kppm.

In further examples, additional correlations of slope (A) and intercept (B) were developed for various drilling fluid densities. In some embodiments, correlations may then be developed between oil volume content and slope (A) or intercept (B) and density. These correlations may be used in determining oil volume content of an oil-based drilling fluid. The following illustrate example linear equations that were developed that can be used in estimation of oil volume content:

$$\text{Oil vol \%} = -0.0277 \times A + (-0.08013 \times \rho + 0.4025) \quad (7)$$

$$\text{Oil vol \%} = -0.003146 \times A + (-0.07846 \times \rho + 0.3583) \quad (8)$$

Wherein Oil vol. % is oil volume content of the oil-based drilling fluid, A is the slope of logarithmic function fitting to phase angle as function of frequency, and B is the intercept of logarithmic function fitting to phase angle as function of frequency. For this specific example, the logarithmic function fitting to phase angle as function of frequency was at 1 kHz to 2 kHz, but other frequency ranges may be suitable as desired for a particular application. These correlations of equations (7) and (8) were verified by testing of several field oil-based drilling fluids that were contaminated with the same base oil, water, and solids. The oil volume content from equations (7) and (8) were comparable to the values obtained from retort tests as shown in Table 1 below.

TABLE 1

| Sample Fluid | 1 | 2 | 3 | 4 | 5 |
|---|---|---|---|---|---|
| Oil Vol % (retort) | 0.482 | 0.511 | 0.499 | 0.459 | 0.515 |
| Est. Oil Vol % (Eq. 5) | 0.489 | 0.510 | 0.504 | 0.459 | 0.517 |
| Error | 0.71% | −0.08% | 0.45% | −0.05% | 0.14% |
| Est. Oil Vol % | 0.480 | 0.505 | 0.495 | 0.444 | 0.514 |
| Error | −0.19% | −0.60% | −0.38% | −1.55% | −0.18% |

Figure 5:
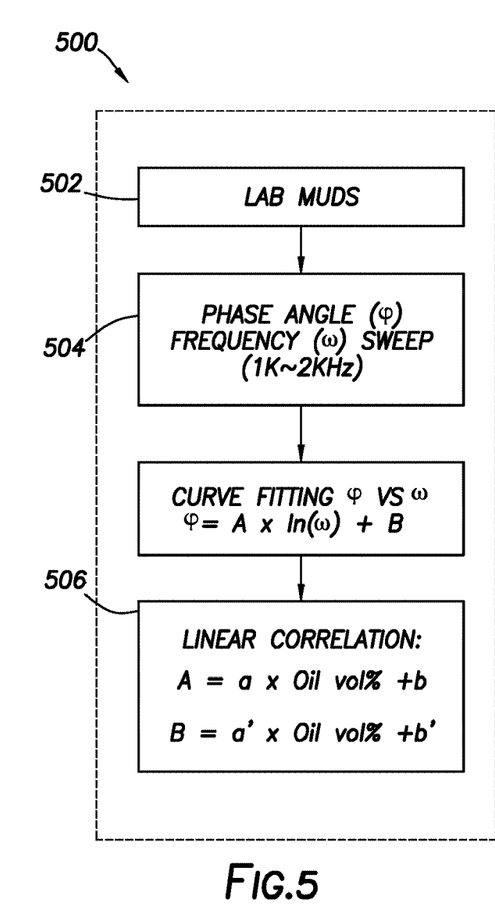
FIG. 5 is an example flow chart illustrating a method of generating a model for estimating oil content for oil-based drilling fluids using impedance phase angle measurement.
Figure 6:
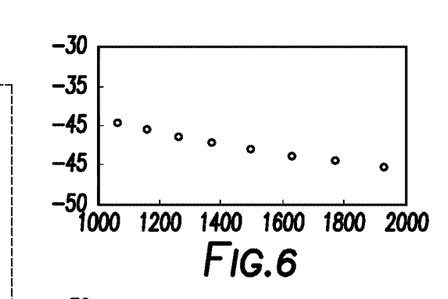
FIG. 6 is an example plot of experimental phase angle versus angular frequency for an oil-based drilling fluid.
Figure 7:
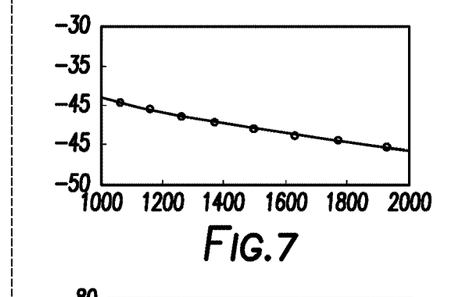
FIG. 7 is an example plot of a logarithmic function fitted to phase angle experimental data of FIG. 6.
Figure 8:
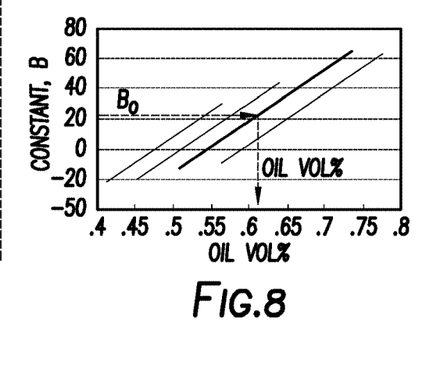
FIG. 8 is an example plot showing example intercepts (B) for various drilling fluid densities as function of oil-to-water ratio.

FIG. 5 is a flow chart illustrating an example method 500 of developing a model that correlates EIS measurements to oil content of an oil-based drilling fluid. The method 500 may include, for example, providing one or more oil-based drilling fluids, as shown at block 502. Providing one or more oil-based drilling fluids may include preparing or otherwise obtaining the one or more oil-based drilling fluids. Where more than one of the oil-based drilling fluids is provided, the oil-based drilling fluids may have similar compositions, for example, salt, base oil, additives; however, the oil-based drilling fluids may vary, in some embodiments, by certain properties, such as density and OWR. The method 500 may further include obtaining EIS measurements of phase angle for a frequency range, as shown at block 504. In some embodiments, EIS may be performed to obtain the phase angle over a specified frequency range (e.g., 1 KHz to 2 KHz). FIG. 6 illustrates example phase angle from EIS measurements over a frequency range of 1 KHz to 2 KHz. The method 500 may further include logarithmic function fitting of the phase angle as a function of frequency, as shown at block 506. In some embodiments, the logarithmic function fitting may obtain simple log-linear expression of the form of equation (3) with slope (A) and intercept (B). FIG. 7 is an example plot of logarithmic function fitting of the phase angle and frequency data from FIG. 6. The method 500 may further include developing linear correlations that relate slope (A) and intercept (B) of the logarithmic function fitting to oil content. By way of example, a linear correlation may be developed of slope (A) as a function of oil content and another linear correlation may developed of intercept (B) as a function of oil content. FIG. 8 is an example plot showing an example linear correlation for different fluid weights that relate intercept (B) to oil content. The method 500 may further include obtaining EIS measurements of the oil-based drilling fluid of phase angle for a frequency range, as shown at block 504. In some embodiments, EIS may be performed on a sample of the oil-based drilling fluid to obtain the phase angle over a specified frequency range (e.g., 1 KHz to 2 KHz).

Figure 9:
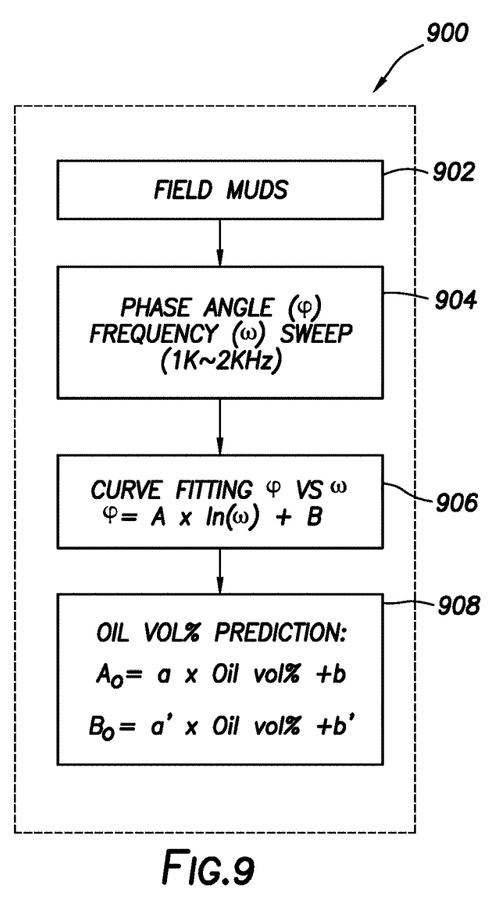
FIG. 9 is an example flow chart illustrating a method of using impedance phase angle measurement in estimation of oil content for oil-based drilling fluids.

FIG. 9 is a flow chart illustrating an example method 900 of estimating oil content of an oil-based drilling mud using EIS measurements. The method 900 may include providing an oil-based drilling fluid as shown at block 902. The oil-based drilling fluid may be provided in a mud pit, on a rig, in a mud plant, in a laboratory, or at any other suitable location. In some embodiments, the oil-based drilling fluid may be provided at a rig site. The oil-based drilling fluid may be a sample of an oil-based drilling fluid being circulated in a wellbore, from example, m e mud pit or any other suitable location, so that the method 900 may be performed in real time. The method 900 may further include obtaining EIS measurements of phase angle for a frequency range, as shown at block 904. In some embodiments, EIS may be performed to obtain the phase angle over a specified frequency range (e.g., 1 KHz to 2 KHz). FIG. 6 illustrates example phase angle from EIS measurements over a frequency range of 1 KHz to 2 KHz. The method 900 may further include logarithmic function fitting of the phase angle as a function of frequency, as shown at block 906. In some embodiments, the logarithmic function fitting may obtain a simple log-linear expression of the form of equation (3) with slope (A) and intercept (B). The method may further include applying the slope (A) and intercept (B) from the logarithmic function fitting to a model that correlates EIS measurements to oil content to obtain an estimate of the oil content for the oil-based drilling fluid, as shown at block 908. For example, the slope (A) may be applied to a model that correlates slope (A) to oil content. By way of further example, the intercept (B) may be applied to a model that correlates intercept (B) to oil content.

Figure 10:
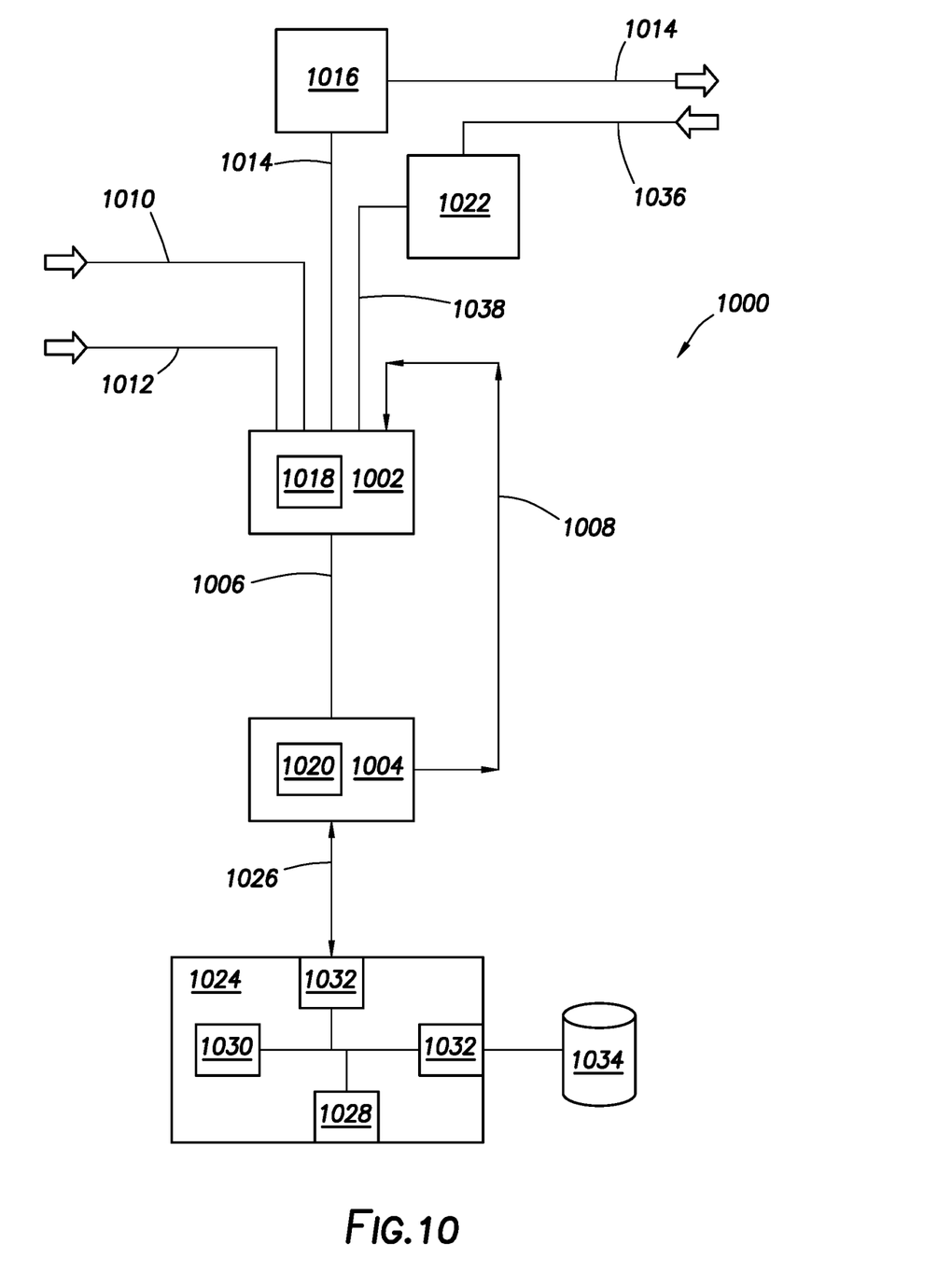
FIG. 10 illustrates a block diagram of a drilling fluid monitoring and handling system.

FIG. 10 illustrates a block diagram of a drilling fluid monitoring and handling system 1000. In some embodiments, the drilling fluid monitoring and handling system 1000 may be configured to measure oil content and determine a desired corrective action if needed. For example, the drilling fluid monitoring and handling system 1000 may determine an amount of additional aqueous fluid, base oil, and/or emulsifier needed in the oil-base drilling fluid and automatically add such additional material. As illustrated, the fluid monitoring and handling system 1000 may generally include a mud pit 1002 and a fluid analysis system 1004. Fluid analysis system 1004 may be operable to perform an EIS measurement of a sample of the oil-based drilling fluid sample and estimate the oil content of the sample based on the EIS measurement. The techniques described previously herein may be used in estimation of the oil content. A sample of the oil-based drilling fluid from the mud pit 1002 may be fed via a mud pit line 1006 to the fluid analysis system 1004. The fluid analysis system 1004 may analyze the sample of oil-based drilling fluid using the example method disclosed above, for example, with respect to FIGS. 1-9. After fluid analysis, the portion of the drilling fluid may be returned to mud pit 1002 via a return line 1008.

The mud pit 1002 may be any vessel suitable for holding an oil-based drilling fluid. For example, the mud pit 1002 may include a container such as a drum or tank, or a series of containers that may or may not be connected. The mud pit 1002 may be supplied with the oil-based drilling fluid from an initial drilling fluid supply line 1010 that provides an initial supply of oil-based drilling fluid to the mud pit 1002. However, the initial supply of oil-based drilling fluid does not imply that the oil-based drilling fluid has not been recycled or circulated in a wellbore, but simply indicates that this supply is not presently being circulated or otherwise used in the wellbore.

Drilling fluid additives (e.g., base oil, aqueous liquid, weighting agents, emulsifying agents, clay inhibitors, clay, viscosifiers, etc.) may be added via a drilling fluid additive supply line 1012 to the mud pit 1002 (or other suitable location), if desired, and based on the analysis provided by the fluid analysis system 1004. Alternatively or additionally, in an example, the results of the analysis may be used to modify the manufacturing process of the oil-based drilling fluid. For example, additional base oil and/or aqueous fluid may be added to the oil-based drilling fluid in response to the estimated oil content. After the drilling fluid additives have been added to the oil-based drilling fluid, the oil-based drilling fluid may be sent to the wellbore for use in drilling operations via a wellbore line 1014 by way of mud pump 1016.

The mud pit 1002 may include a mixing system 1018 to mix the contents of the mud pit 1002 as well as any drilling fluid additives. For instance, the mixing system 1018 may mix the drilling fluid in the mud pit 1002 with drilling fluid from the initial drilling fluid supply line 1010, drilling fluid from the return line 1008, drilling fluid additives, additional base oils, aqueous fluids or combinations thereof. In general, the mixing system 1018 may be configured to prevent solids within the drilling fluid from settling. The mixing system 1018 may use any suitable mixing technique for mixing of the drilling fluid. For instance, the mixing system 1018 may include a static mixer, dynamic mixer, or other suitable mixer. The mud pit 1002 may further include suitable pumping equipment (not shown) to pump the drilling fluid in the mud pit 1002 to the fluid analysis system 1004 via mud pit line 1006.

The fluid analysis system 1004 may analyze the sample of the drilling fluid in a continuous or non-continuous manner, as desired, and based on whether flow through fluid analysis system 1004 is continuous or non-continuous. In some embodiments, the fluid analysis system 1004 may include an EIS system 1020. Although the fluid analysis system 1004 is shown at the mud pit 1002, examples disclosed herein contemplate the placement of fluid analysis system 1004 at any point in the fluid monitoring and handling system 1000. For example, fluid analysis system 1004 (or a portion thereof) may alternatively be placed in a fluid reconditioning system 1022 (discussed below), the mud pit 1002, as well as within the wellbore or in an exit conduit from the wellbore. As such, examples disclosed herein contemplate measuring the impedance at any point in the drilling fluid handling process, so that the drilling fluid may be monitored and/or subsequently adjusted as desired.

The analysis performed by fluid analysis system 1004 may be performed in collaboration with a computer system 1024 communicably coupled thereto. As illustrated, the computer system 1024 may be an external component of the fluid analysis system 1004, however, the computer system 1024 may alternatively include an internal component of the fluid analysis system 1004, without departing from the scope of the disclosure. The computer system 1024 may be connected to the fluid analysis system 1004 via a communication link 1026. The communication link 1026 may include a direct (wired) connection, a private network, a virtual private network, a local area network, a WAN (e.g., an Internet-based communication system), a wireless communication system (e.g., a satellite communication system, telephones), any combination thereof, or any other suitable communication link.

The computer system 1024 may be any suitable data processing system including, but not limited to, a computer, a handheld device, or any other suitable device. The computer system 1024 may include a processor 1028 and a non-transitory computer readable storage medium 1030 communicatively coupled to the processor 1028. The processor 1028 may include one central processing unit or may be distributed across one or more processors in one or more locations. Examples of a non-transitory computer readable storage medium 1030 include random-access memory (RAM) devices, read-only memory (ROM) devices, optical devices (e.g., CDs or DVDs), disk drives, and the like. The non-transitory computer readable storage medium 1030 may store computer readable program code that may be executed by the processor 1028 to process and analyze the measurement data generated by fluid analysis system 1004, adjust the parameters of the fluid monitoring and handling system 1000, and/or operate a part or whole of the fluid monitoring and handling system 1000. Further, from the EIS measurements of the oil-based drilling fluid measured by the fluid analysis system 1004, the program code may be executed by the processor 1028 to determine an estimate of the oil content. Based on the oil content, for example, the fluid analysis system 1004 may add additional base oil and/or aqueous fluid to the oil-based drilling fluid.

The computer system 1024 may further include one or more input/output ("I/O") interface(s) 1032 communicatively coupled to the processor 1028. The I/O interface(s) 1032 may be any suitable system for connecting the computer system 1024 to a communication link, such as a direct connection, a private network, a virtual private network, a local area network, a wide area network ("WAN"), a wireless communication system, or combinations thereof; a storage device, such as storage 1034; an external device, such as a keyboard, a monitor, a printer, a voice recognition device, or a mouse; or any other suitable system. The storage 1034 may store data required by the fluid analysis system 1004 for performing fluid analysis. For instance, the storage 1034 may store a collection of equivalent circuit models that may be used during the EIS analysis. The storage 1034 may be or include compact disc drives, floppy drives, hard disks, flash memory, solid-state drives, and the like. Those of ordinary skill in the art will appreciate that suitable data processing systems may include additional, fewer, and/or different components than those described for computer system 1024.

Data processing and analysis software native to the fluid analysis system 1004 and/or installed on the computer system 1024 may be used to analyze the data generated by fluid analysis system 1004. This procedure may be automated such that the analysis happens without the need for operator input or control. Further, the operator may select from several previously input parameters or may be able to recall previously measured data. Any of the data may be transferred and/or stored on an external memory device (e.g., a USB drive), if desired.

With continued reference to FIG. 10, the drilling fluid may delivered to a wellbore from mud pit 1002 by way of mud pump 1016 via wellbore line 1014. The mud pump 1016 may be any type of pump or pumping system useful for circulating a drilling fluid into a subterranean formation under a sufficient pressure. The drilling fluid that has been circulated within the wellbore may be returned to the mud pit 1002 via a circulated drilling fluid return line 1036 and provided to a fluid reconditioning system 1022 to condition the circulated drilling fluid prior to returning it to the mud pit 1002. The fluid reconditioning system 1022 may be or include one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. The fluid reconditioning system 1022 may further include one or more sensors, gauges, pumps, compressors, and the like used to monitor, regulate, and/or recondition the drilling fluid and various additives added thereto. After the drilling fluid has been reconditioned, the drilling fluid may be returned to the mud pit 1002 via the reconditioned fluid line 1038.

Figure 11:
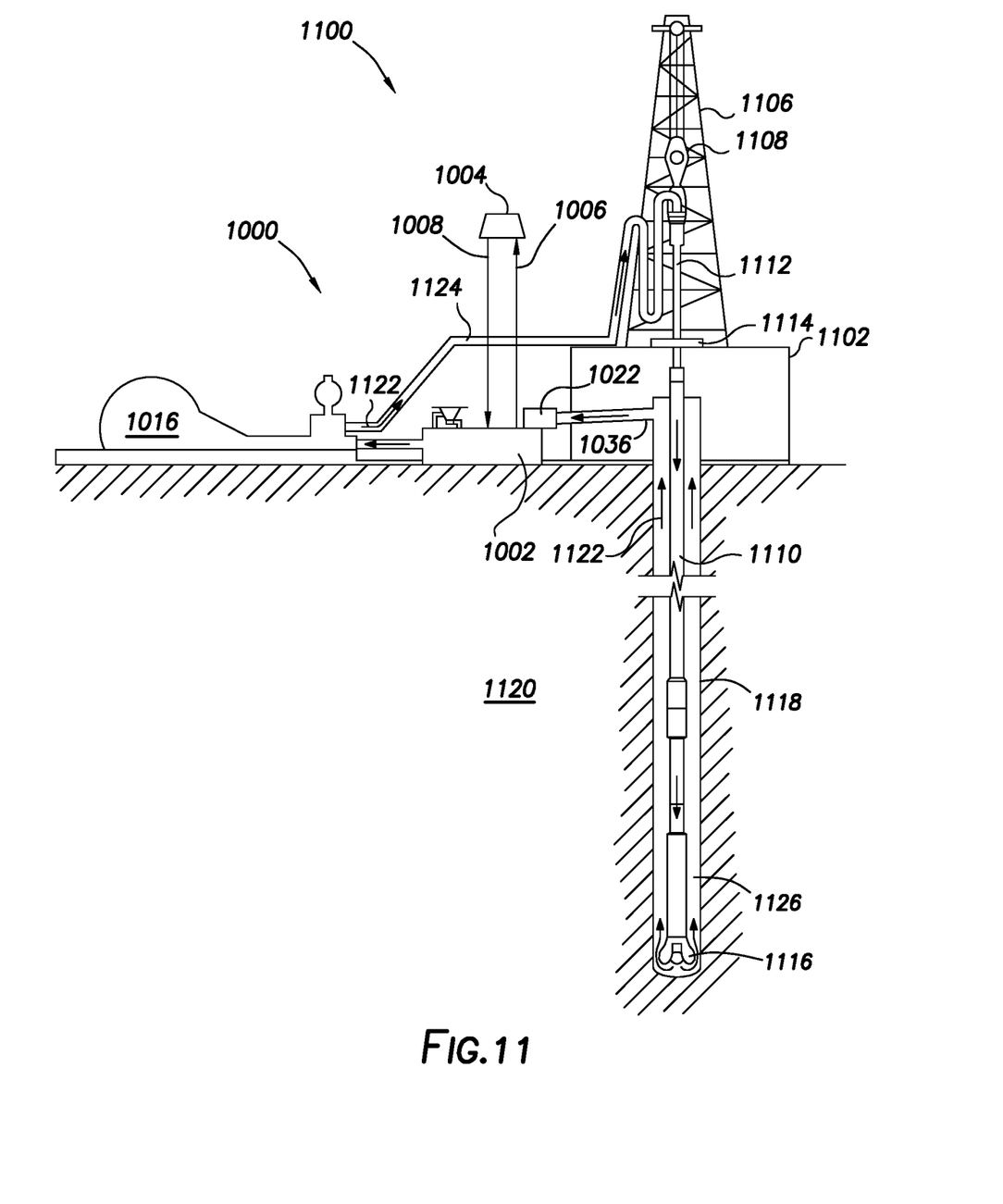
FIG. 11 illustrates an example drilling assembly that incorporates the drilling fluid monitoring and handling system of FIG. 10.

FIG. 11 illustrates an example of a drilling system 1100 that may employ the fluid monitoring and handling system 1000 of FIG. 10 described herein to monitor oil content. It should be noted that while FIG. 11 generally depicts a land-based drilling system, those skilled in the art will readily recognize that the principles described herein are equally applicable to subsea drilling operations that employ floating or sea-based platforms and rigs, without departing from the scope of the disclosure.

As illustrated, the drilling system 1100 may include a drilling platform 1102 that supports a derrick 1106 having a traveling block 1108 for raising and lowering a drill string 1110. The drill string 1110 may include, but is not limited to, drill pipe and coiled tubing, as generally known to those skilled in the art. A kelly 1112 may support the drill string 1110 as it may be lowered through a rotary table 1114. A drill bit 1116 may be attached to the distal end of the drill string 1110 and may be driven either by a downhole motor and/or via rotation of the drill string 1110 from the well surface. Without limitation, the drill bit 1116 may include, roller cone bits, PDC bits, natural diamond bits, any hole openers, reamers, coring bits, and the like. As the drill bit 1116 rotates, it may create a wellbore 1118 that penetrates various subterranean formations 1120.

The drilling system 1010 may further include the fluid monitoring and handling system 1000 as generally described herein. The mud pump 1016 of the fluid monitoring and handling system 1000 representatively includes any conduits, pipelines, trucks, tubulars, and/or pipes used to fluidically convey the oil-based drilling fluid 1122 downhole, any pumps, compressors, or motors (e.g., topside or downhole) used to drive the oil-based drilling fluid 1122 into motion, any valves or related joints used to regulate the pressure or flow rate of the oil-based drilling fluid 1122, and any sensors (e.g., pressure, temperature, flow rate, etc.), gauges, and/or combinations thereof, and the like.

The mud pump 1016 may circulate may circulate the oil-based drilling fluid 1122 through a feed pipe 1124 and to the kelly 1112, which conveys the oil-based drilling fluid 1122 downhole through the interior of the drill string 1110 and through one or more orifices in the drill bit 1116. The oil-based drilling fluid 1122 may then be circulated back to the surface via an annulus 1126 defined between the drill string 1110 and the walls of the wellbore 1118. At the surface, the recirculated or spent oil-based drilling fluid 1122 may be conveyed to the fluid reconditioning system 1022 via a circulated drilling fluid return line 1036. After passing through the fluid reconditioning system 1022, a "cleaned" oil-based drilling fluid 1122 may be deposited into a nearby mud pit 1002. While illustrated as being arranged at the outlet of the wellbore 1118 via the annulus 1126, those skilled in the art will readily appreciate that the fluid reconditioning system 1022 may be arranged at any other location in the drilling system 1100 to facilitate its proper function, without departing from the scope of the scope of the disclosure.

Referring still to FIG. 11, the fluid monitoring and handling system 1000 may further include the fluid analysis system 1004, which may be disposed on a skid supported on the drilling platform 1102. The fluid analysis system 1004 may, for example, continuously or intermittently measure oil content of the oil-based drilling fluid 1122. As illustrated, the oil-based drilling fluid 1122 may be taken from the mud pit 1002 via the mud pit line 1006 and an analyzed drilling fluid may be returned to the mud pit 1002 via the return line 1008. Alternatively, the oil content may be measured at fluid reconditioning system 1022, or at any other suitable location, even while in the wellbore 1118 if desired.

Thus, the fluid monitoring and handling system 1000 may advantageously measure the oil content using the example method disclosed herein. The fluid monitoring and handling system 1000 may also generate automatic warnings to the personnel when the oil content deviate from preset safety margins and/or automatically add additional amounts of the base oil and/or aqueous fluid to the oil-based drilling fluid when the oil content deviates from preset safety margins.

Figure 12:
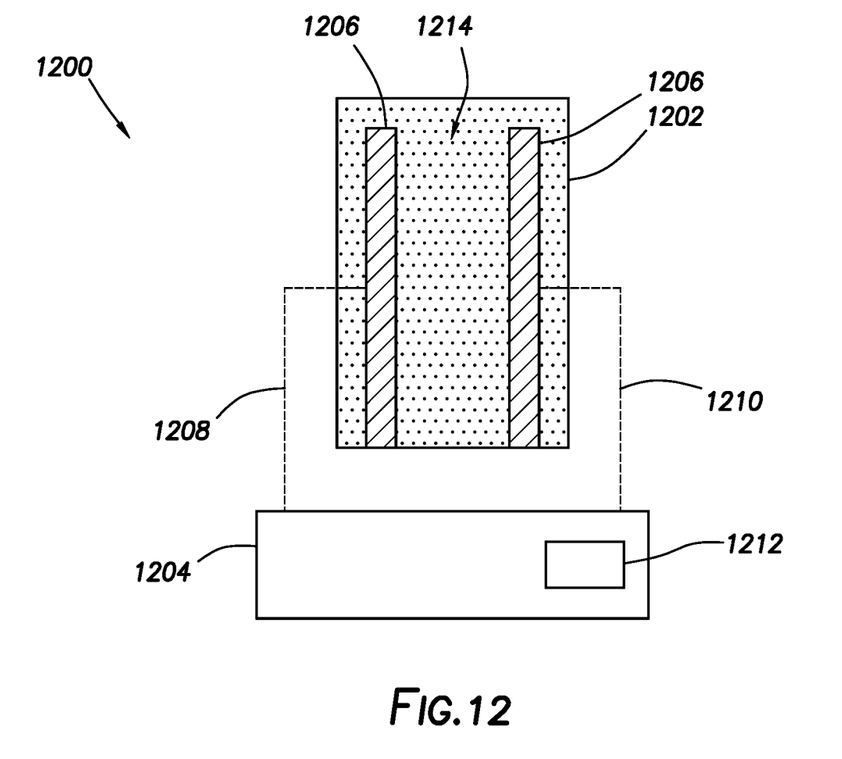
FIG. 12 illustrates an example embodiment of an electrical impedance spectroscopy fluid analysis system.

FIG. 12 illustrates an EIS fluid analysis system 1200 that may be used to measure impedance for a drilling fluid. As illustrated, the EIS fluid analysis system 1200 may include a container 1202 and an electronics device 1204 for measuring impedance, including, but not limited to impedance analyzers. LCR meters, and EIS analyzers. Container 1202 may be any suitable container for holding a sample fluid 1214. A pair of electrodes 1206 may be disposed in container 1202. Electrodes 1206 may have any suitable configuration, including, not limited to, plates, cylinders, and rods, among others. As illustrated, electrodes 1206 may be generally parallel to one another. Electrodes 1206 are considered generally parallel where they converge or diverge by no more than 5'. In addition, electrodes 1206 are shown disposed in container 1202 in a vertical configuration. While electrodes 1206 are shown in the vertical configuration, it should be understood that electrodes 1206 may be disposed in container 1202 in other configurations, including, but not limited to, horizontal and angled configurations. It should understood that the electrodes 1206 should be considered in a vertical configuration where the longitudinal axis of the electrodes 1206 extend at angle of from 85° to 95° with respect to the horizontal plane. In one example, a gap may be disposed between electrodes 1206 ranging from about 0.1 inch (0.25 cm) to about 1 inch (2.5 cm), about 0.1 inches (0.25 cm) to about 0.5 inch (1.25 cm), or about 0.5 inch (1.25 cm) to about 1 inch (2.5 cm). For example, electrodes 1206 may a gap of about 0.19 inches (0.48 cm).

Electronics device 1204 may be in signal communication with plates 1204. As illustrated, lines 1208, 1210 may couple electrodes 1206 to electronics device 1204. Electronics device 1204 may measure impedances of sample fluid 1214. The electronics device 1204 may include a signal generator 1212. As illustrated, signal generator 1212 is shown as a component of electronics device 1204, but signal generator 1212 may also be separate from electronics device 1204. Signal generator 1212 by way of EIS analyzer, 1204 for example, may apply an electric signal, such as an AC signal, to electrodes 1206 so that the electric signal pass through sample fluid 1214 in container 1202. Lines 1208, 1210 may allow electronics device 1204 to capture measurements of sample fluid 1214 during application of the electrical signal. By way of example, the electronics device 1204 may determine current through sample fluid 1214 in container 1202, the potential difference across the sample fluid 1214 in container 1202, and/or the phase angle θ. From these measurements of phase angle, the oil content of the sample fluid 1214 may be determined, for example, as described herein.

Accordingly, this disclosure describes systems and methods that are directed to measuring oil content of an oil-based drilling fluid. Without limitation, the systems and methods may further be characterized by one or more of the following statements:

Statement 1: A method for measuring oil content of an oil-based drilling fluid. The method may include providing a sample of the oil-based drilling fluid. The method may include performing electro impedance spectroscopy on the sample by a process that comprises applying an alternating electric current to the sample and measuring a response of sample to obtain electro impedance spectroscopy measurements. The method may further include determining an estimate of the oil content of the sample based, at least partially on the electro impedance spectroscopy measurements.

Statement 2: The method of statement 1, wherein the oil-based drilling fluid is an invert emulsion that includes an internal aqueous phase dispersed in an external oil phase.

Statement 3: The method of statement 1 or 2, wherein the measuring a response of the sample includes placing the sample in a container and applying the alternating current electric to the sample in the container.

Statement 4: The method of any one of statements 1 to 3, wherein the measuring a response includes measuring impedance of the sample.

Statement 5: The method of any one of statements 1 to 4, wherein the providing the sample includes feeding the sample from a mud pit containing at least a portion of the oil-based drilling fluid to a container in a fluid analysis system fluidically coupled to the mud pit by way of a mud pit line.

Statement 6: The method of any one of statements 1 to 5, wherein the determining an estimate of the oil content includes determining phase angle for a range of angular frequency and then logarithmic function fitting the phase angle for the range of the angular frequency to obtain a log-linear expression with slope (A) and intercept (B).

Statement 7: The method of statement 6, wherein the range of the angular frequency is from about 1 kilohertz to about 2 kilohertz.

Statement 8: The method of statement 6 or 7, wherein the determining an estimate of the oil content includes applying the slope (A) to a model that correlates the slope (A) to drilling fluid oil content.

Statement 9: The method of any one of statements 6 to 8, wherein the determining an estimate of the oil content includes applying the intercept (B) to a model that correlates the intercept (B) to drilling fluid oil content.

Statement 10: The method of any one of statements 1 to 9, wherein determining an estimate of the oil content includes applying the electro impedance spectroscopy measurements to a model that correlates the electro impedance spectroscopy measurements to drilling fluid oil content.

Statement 11: The method of any one of statements 1 to 10, wherein a model that correlates electro impedance spectroscopy measurements to drilling fluid oil content is used in determining the estimate. The method may further include developing the model. The model may be developed by a process that includes providing one or more oil-based drilling fluids having known oil content. The model may be developed by a process that includes obtaining electro impedance spectroscopy measurements of phase angle for a frequency range. The model may be developed by a process that further includes logarithmic function fitting of the phase angle as a function of frequency to obtain a log-linear expression of the phase angle as the function of the frequency that has a slope (A) and intercept (B). The model may be developed by a process that further includes developing linear correlations that relate at least one of slope (A) or intercept (B) to drilling fluid oil content to provide the model.

Statement 12: The method of any one of statements 1 to 11, further including adding base oil and/or aqueous fluid to the oil-based drilling fluid in response to the estimate of the oil content.

Statement 13: The method of statement 12, further including sending a signal from a computer system such that the base oil and/or aqueous fluid is automatically added to the oil-based drilling fluid.

Statement 14: The method of statement 1, wherein the providing the sample includes feeding the sample from a mud pit containing at least a portion of the oil-based drilling fluid to a container in a fluid analysis system fluidically coupled to the mud pit by way of a mud pit line, wherein the determining an estimate of the oil content includes determining phase angle for a range of the angular frequency from about 1 kilohertz to about 2 kilohertz and then logarithmic function fitting the phase angle for the range of the angular frequency to obtain a log-linear expression with slope (A) and intercept (B), and wherein the determining an estimate of the oil content includes at least one of (i) applying the slope (A) to a model that correlates the slope (A) to drilling fluid oil content; and/or (ii) applying the intercept (B) to a model that correlates the intercept (B) to drilling fluid oil content.

Statement 15: A drilling method that includes circulating an oil-based drilling fluid through a wellbore while drilling the wellbore. The drilling method may further include feeding a sample of the oil-based drilling fluid through a line to a container in a fluid analysis system fluidically coupled to a drilling system while the circulating is continuously performed. The drilling method may further include performing electro impedance spectroscopy on the sample by a process that includes applying an alternating electric current to the sample and measuring a response of sample to obtain electro impedance spectroscopy measurements. The drilling method may further include determining an estimate of the oil content of the sample based, at least partially on the electro impedance spectroscopy measurements. The drilling method may further include adding base oil and/or aqueous fluid to the oil-based drilling fluid in response to the estimate.

Statement 16: The method of statement 15, wherein the determining an estimate of the oil content includes determining phase angle for a range of the angular frequency from about 1 kilohertz to about 2 kilohertz, then logarithmic function fitting the phase angle for the range of the angular frequency to obtain a log-linear expression with slope (A) and intercept (B), and al least one of (i) applying the slope (A) to a model that correlates the slope (A) to drilling fluid oil content; and/or (ii) applying the intercept (B) to a model that correlates the intercept (B) to drilling fluid oil content.

Statement 17: A drilling system may include a drill string, a drill bit attached to a distal end of the drill string, and a fluid monitoring and handling system. The fluid monitoring and handling system may include a mud pit operable to receive an oil-based drilling fluid from a wellbore. The fluid monitoring and handling system may include a mud pump operable to circulate the oil-based drilling fluid. The fluid monitoring and handling system may further include a fluid analysis system. The fluid analysis system may include a sample container for a sample of oil-based drilling fluid and an electronics device for measuring impedance of the sample. The fluid monitoring and handling system may further include a computer system in signal communication with the fluid analysis system, wherein the computer system may include a processor and a non-transitory computer readable storage medium that when executed by the processor causes the computer system to send a signal to initiate an electro impedance spectroscopy measurement and estimate an oil content of the sample based, at least partially, on the electro impedance spectroscopy measurement.

Statement 18: The drilling system of statement 17, wherein a mud pit line fluidically couples the mud pit and the sample container.

Statement 19: The drilling system of statement 17 or 18, wherein the non-transitory computer readable storage medium is further configured to cause the computer system to send a signal to cause addition of base oil and/or aqueous fluid to the oil-based drilling fluid.

Statement 20: The drilling system of any one of statements 17 to 19, wherein the non-transitory computer readable storage medium is further configured to cause the computer system to determine an estimate of the oil content, wherein the estimate of the oil content is determined by the non-transitory computer readable storage medium being further configured to cause the computer system to determine phase angle for a range of the angular frequency, then logarithmic function fit the phase angle for the range of the angular frequency to obtain a log-linear expression with slope (A) and intercept (B), and at least one of (i) apply the slope (A) to a model that correlates the slope (A) to drilling fluid oil content, or (ii) apply the intercept (B) to a model that correlates the intercept (B) to drilling fluid oil content.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in terms of "including," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted.

What is claimed is:

1. A method comprising:
   providing a sample of an oil-based drilling fluid;
   performing electro impedance spectroscopy on the sample by a process that comprises applying an alternating electric current to the sample and measuring a response of sample to obtain electro impedance spectroscopy measurements; and
   determining an estimate of oil content of the sample based, at least partially on the electro impedance spectroscopy measurements, by determining phase angle for a range of angular frequencies, wherein the phase angle is a function of an oil-to-water ratio and low-gravity solids.

2. The method of claim 1, wherein the oil-based drilling fluid is an invert emulsion comprising an internal aqueous phase dispersed in an external oil phase.

3. The method of claim 1, wherein the measuring a response of the sample comprises placing the sample in a container and applying the alternating current electric to the sample in the container.

4. The method of claim 1, wherein the measuring a response comprises measuring impedance of the sample.

5. The method of claim 1, wherein the providing the sample comprises feeding the sample from a mud pit containing at least a portion of the oil-based drilling fluid to a container in a fluid analysis system fluidically coupled to the mud pit by way of a mud pit line.

6. The method of claim 1, wherein the determining an estimate of the oil content further comprises logarithmic function fitting the phase angle for the range of the angular frequency to obtain a log-linear expression with slope (A) and intercept (B).

7. The method of claim 6, wherein the range of the angular frequency is from about 1 kilohertz to about 2 kilohertz.

8. The method of claim 6, wherein the determining an estimate of the oil content comprises applying the slope (A) to a model that correlates the slope (A) to drilling fluid oil content.

9. The method of claim 6, wherein the determining an estimate of the oil content comprises applying the intercept (B) to a model that correlates the intercept (B) to drilling fluid oil content.

10. The method of claim 1, wherein determining an estimate of the oil content comprises applying the electro impedance spectroscopy measurements to a model that correlates the electro impedance spectroscopy measurements to drilling fluid oil content.

11. The method of claim 1, wherein a model that correlates electro impedance spectroscopy measurements to drilling fluid oil content is used in determining the estimate, wherein the method further comprises developing the model through a process comprising:
  providing one or more oil-based drilling fluids having known oil content;
  obtaining electro impedance spectroscopy measurements of phase angle for a frequency range;
  logarithmic function fitting of the phase angle as a function of frequency to obtain a log-linear expression of the phase angle as the function of the frequency that has a slope (A) and intercept (B); and
  developing linear correlations that relate at least one of slope (A) or intercept (B) to drilling fluid oil content to provide the model.

12. The method claim 1, further comprising adding base oil and/or aqueous fluid to the oil-based drilling fluid in response to the estimate of the oil content.

13. The method of claim 12, further comprising sending a signal from a computer system such that the base oil and/or aqueous fluid is automatically added to the oil-based drilling fluid.

14. The method of claim 1:
  wherein the providing the sample comprises feeding the sample from a mud pit containing at least a portion of the oil-based drilling fluid to a container in a fluid analysis system fluidically coupled to the mud pit by way of a mud pit line;
  wherein the determining an estimate of the oil content comprises determining phase angle for a range of the angular frequency from about 1 kilohertz to about 2 kilohertz and then logarithmic function fitting the phase angle for the range of the angular frequency to obtain a log-linear expression with slope (A) and intercept (B); and
  wherein the determining an estimate of the oil content comprises at least one of (i) applying the slope (A) to a model that correlates the slope (A) to drilling fluid oil content; and/or (ii) applying the intercept (B) to a model that correlates the intercept (B) to drilling fluid oil content.

15. A drilling method, comprising:
  circulating an oil-based drilling fluid through a wellbore while drilling the wellbore
  feeding a sample of the oil-based drilling fluid through a line to a container in a fluid analysis system fluidically coupled to a drilling system while the circulating is continuously performed;
  performing electro impedance spectroscopy on the sample by a process that comprises applying an alternating electric current to the sample and measuring a response of sample to obtain electro impedance spectroscopy measurements;
  determining an estimate of the oil content of the sample based, at least partially on the electro impedance spectroscopy measurements, by determining phase angle for a range of angular frequencies, wherein the phase angle is a function of an oil-to-water ratio and low-gravity solids; and
  adding base oil and/or aqueous fluid to the oil-based drilling fluid in response to the estimate.

16. The method of claim 15, wherein the determining an estimate of the oil content comprises determining phase angle for a range of the angular frequency from about 1 kilohertz to about 2 kilohertz, then logarithmic function fitting the phase angle for the range of the angular frequency to obtain a log-linear expression with slope (A) and intercept (B), and at least one of (i) applying the slope (A) to a model that correlates the slope (A) to drilling fluid oil content; and/or (ii) applying the intercept (B) to a model that correlates the intercept (B) to drilling fluid oil content.

17. A drilling system comprising:
  a drill string;
  a drill bit attached to a distal end of the drill string; and
  a fluid monitoring and handling system comprising
    a mud pit operable to receive an oil-based drilling fluid from a wellbore;
    a mud pump operable to circulate the oil-based drilling fluid; and
    a fluid analysis system comprising a sample container for a sample of oil-based drilling fluid, an electronics device for measuring impedance of the sample; and
    a computer system in signal communication with the fluid analysis system, wherein the computer system comprises a processor and a non-transitory computer readable storage medium that when executed by the processor causes the computer system to send a signal to initiate an electro impedance spectroscopy measurement and estimate an oil content of the sample based, at least partially, on the electro impedance spectroscopy measurement, by determining phase angle for a range of angular frequencies, wherein the phase angle is a function of an oil-to-water ratio and low-gravity solids.

18. The drilling system of claim 17, wherein a mud pit line fluidically couples the mud pit and the sample container.

19. The drilling system of claim 17, wherein the non-transitory computer readable storage medium is further configured to cause the computer system to send a signal to cause addition of base oil and/or aqueous fluid to the oil-based drilling fluid.

20. The drilling system of claim 17, wherein the non-transitory computer readable storage medium is further configured to cause the computer system to determine an estimate of the oil content, wherein the estimate of the oil content is determined by the non-transitory computer readable storage medium being further configured to cause the computer system to determine phase angle for a range of the angular frequency, then logarithmic function fit the phase angle for the range of the angular frequency to obtain a log-linear expression with slope (A) and intercept (B), and at least one of (i) apply the slope (A) to a model that correlates the slope (A) to drilling fluid oil content, or (ii) apply the intercept (B) to a model that correlates the intercept (B) to drilling fluid oil content.

\* \* \* \* \*